US008383617B2

(12) United States Patent
Wilson et al.

(10) Patent No.: US 8,383,617 B2
(45) Date of Patent: Feb. 26, 2013

(54) TREATMENT OF PROTEIN AGGREGATION DISEASES (75) Inventors: Stuart Mark Wilson, London (GB); Christopher John Stanley, London (GB)

(73) Assignee: PAD Pharma Limited, London (GB)

(*) Notice: Subject to any disclaimer, the term of this patent is extended or adjusted under 35 U.S.C. 154(b) by 540 days.

(21) Appl. No.: 12/525,381

(22) PCT Filed: Jan. 30, 2008

(86) PCT No.: PCT/EP2008/051134
§ 371 (c)(1),
(2), (4) Date: Oct. 14, 2009

(87) PCT Pub. No.: WO2008/092898
PCT Pub. Date: Aug. 7, 2008

(65) Prior Publication Data
US 2010/0035859 A1 Feb. 11, 2010

(30) Foreign Application Priority Data
Feb. 1, 2007 (GB) .................................. 0701970.6
Mar. 2, 2007 (GB) .................................. 0704105.6

(51) Int. Cl.
*A61K 31/135* (2006.01)
*A61K 31/382* (2006.01)
*A61K 31/496* (2006.01)
*A61K 31/5415* (2006.01)
*A61K 31/55* (2006.01)
*A61K 31/554* (2006.01)

(52) U.S. Cl. ................ 514/211.13; 514/217; 514/225.5; 514/225.8; 514/226.2; 514/252.13; 514/437; 514/654

(58) Field of Classification Search ............. 514/211.13, 514/217, 225, 5, 8, 226, 2, 252, 13, 437, 514/654
See application file for complete search history.

(56) References Cited

U.S. PATENT DOCUMENTS

| 2,554,736 | A |   | 5/1951 | Haefliger et al. |
| 3,058,979 | A |   | 10/1962 | Ullyot et al. |
| 3,953,566 | A |   | 4/1976 | Gore |
| 4,310,524 | A | * | 1/1982 | Wiech et al. ............... 514/217 |
| 5,597,826 | A |   | 1/1997 | Howard et al. |
| 6,030,984 | A |   | 2/2000 | Trottmann et al. |
| 6,277,852 | B1 |   | 8/2001 | Howard |
| 2002/0091119 | A1 |   | 7/2002 | Howard |
| 2002/0161002 | A1 | * | 10/2002 | Epstein et al. ............... 514/220 |
| 2003/0108551 | A1 |   | 6/2003 | Nicolau et al. |
| 2004/0092569 | A1 |   | 5/2004 | Demaine et al. |

FOREIGN PATENT DOCUMENTS

| EP | 0 275 668 | 7/1988 |
| FR | EP1470818 A1 * | 10/2004 |
| WO | WO 96/04915 | 2/1996 |
| WO | WO 97/03067 | 1/1997 |
| WO | WO 97/16191 | 5/1997 |
| WO | WO 99/25339 | 5/1999 |
| WO | WO 00/59504 | 10/2000 |
| WO | WO 01/12174 | 2/2001 |
| WO | WO 02/38142 | 5/2002 |
| WO | WO 03/073106 | 9/2003 |
| WO | WO 2004/045718 | 6/2004 |
| WO | WO 2004/058258 | 7/2004 |
| WO | WO2004/095031 A1 * | 11/2004 |
| WO | WO 2005/063254 | 7/2005 |
| WO | WO 2006/007864 | 1/2006 |
| WO | WO 2006/017614 | 2/2006 |

OTHER PUBLICATIONS

Golden Dementia and Alzheimer's Disease. Clinical & Health Affairs, Minnesota Medicine, Jan. 1995 vol. 78, pp. 25-29.*
Laabich et al. Neuroprotective effect of AIP on N-methyl-D-aspartate-induced cell death in retinal neurons. Molecular Brain Research 85 (2000) 32-40.*
International Search Report for PCT/EP2008/051134 dated Feb. 5, 2008.
Barret, et al., "Evaluation of Quinacrine Treatment for Prion Diseases", Journal of Virology, vol. 77, No. 15, Aug. 2003, pp. 8462-8469.
Cummings, et al., "Guidelines for Managing Alzheimer's Disease: Part II. Treatment", American Family Physician, vol. 65, No. 12, Jun. 15, 2002, pp. 2525-2534.
DeMarco, et al., "From conversion to aggregation: Protofibril formation of the prion protein", PNAS, vol. 101, No. 8, Feb. 24, 2004, pp. 2293-2298.
Dervaux, et al., Abstract of "Psychiatric manifestations of a new variant of Creutzfeldt-Jakob disease. Apropos of a case", Encephale, vol. 27(2), Mar.-Apr. 2001, 1 page.
De Felice, et al., "β-Amyloid Production, Aggregation, and Clearance as Targets for Therapy in Alzheimer's Disease", Cellular and Molecular Neurobiology, vol. 22, Nos. 5/6, Dec. 2002, pp. 545-563.
Glegg, et al al., "Pharmacological studies of fluphenazine and nortriptyline in combination in man", Letters to the Editor, J. Pharm. Pharmac., vol. 23, 1971, pp. 133-134.
Gomez-Perez, et al., "Nortriptyline-Fluphenazine vs. Carbamazepine in the Symptomatic Treatment of Diabetic Neuropathy", Archives of Medical Research, vol. 27, No. 4, 1996, pp. 525-529.
Khan, et al., "Inhibition of the type 1 inositol 1,4,5-trisphosphate-sensitive $Ca^{2+}$ channel by calmodulin antagonists", Cellular Signalling, vol. 13, 2001, pp. 57-63.
Klingenstein, et al., "Tricyclic antidepressants, quinacrine and a novel, synthetic chimera thereof clear prions by destabilizing detergent-resistant membrane compartments", Journal of Neurochemistry, vol. 98, 2006, pp. 748-759.
Kocisko, et al., "New Inhibitors of Scrapie-Associated Prion Protein Formation in a Library of 2,000 Drugs and Natural Products", Journal of Virology, vol. 77, No. 19, Oct. 2003, pp. 10288-10294.
Kocisko, et al., "Evaluation of new cell culture inhibitors of protease-resistant prion protein against scrapie infection of mice", Journal of General Virology, vol. 85, 2004, pp. 2479-2483.

(Continued)

*Primary Examiner* — Jennifer M Kim
(74) *Attorney, Agent, or Firm* — Pillsbury Winthrop Shaw Pittman LLP (57) ABSTRACT

A method of treatment for the prevention or therapy of a protein aggregation disease includes the administration in combination of a first active medicament and a second active medicament, wherein the first active medicament is active to impede aggregation of amyloid protein and the second active medicament is active to disaggregate previously formed aggregates of amyloid protein.

5 Claims, 4 Drawing Sheets

OTHER PUBLICATIONS

Kocisko, et al., Abstract of "Identification of New Cell-Culture Inhibitors of PrP-res and their Testing Against Scrapie Infection in Mice", Ames conference 2004, p. 49.

Korth, et al., "Acridine and phenothiazine derivatives as pharmacotherapeutics for prion disease", PNAS, vol. 98, No. 17, Aug. 14, 2001, pp. 9836-9841.

Kuner, et al., "Controlling Polymerization of β-Amyloid and Prion-derived Peptides with Synthetic Small Molecule Ligands", The Journal of Biological Chemistry, vol. 275, No. 3, Jan. 21, 2000, pp. 1673-1678.

Lopez, et al., "Patterns of Change in the Treatment of Psychiatric Symptoms in Patients With Probable Alzheimer's Disease From 1983 to 2000", J Neuropsychiatry Clin Neurosci, vol. 15:1, 2003, pp. 67-73.

May, "Commentary: Amyloid-β Deposits: Can You Take Them to the Bank?", Alzheimer's Disease Review 2, 1997, pp. 15-19.

May, et al., "Potent inhibition of scrapie prion replication in cultured cells by bis-acridines", PNAS, vol. 100, No. 6, Mar. 18, 2003, pp. 3416-3421.

Mongin, et al., "Volume-dependent taurine release from cultured astrocytes requires permissive $[Ca^{2+}]_i$ and calmodulin", Am. J. Physiol. 277 (Cell Physiol. 46), 1999, pp. C823-C832.

Moses, et al., "Smooth Muscle Cell Response to Mechanical Injury Involves Intracellular Calcium Release and ERK1/ERK2 Phosphorylation", Experimental Cell Research, vol. 269, 2001, pp. 88-96.

Stevenson, et al., "The Effect of Fluphenazine on Steady State Plasma Levels of Nortriptyline", Letters to the Editors, Brit J Clin Pharmacol, vol. 1, No. 4, 1974, pp. 337-338.

Teri, et al., "Imipramine in the Treatment of Depressed Alzheimer's Patients: Impact on Cognition", Journal of Gerontology: Psychological Sciences, vol. 46, No. 6, 1991, pp. P372-P377.

Terstappen, et al., "Pharmacological characterization of the human small conductance calcium-activated potassium channel hSK3 reveals sensitivity to tricyclic antidepressants and antipsychotic phenothiazines", Neuropharmacology, vol. 40, 2001, pp. 772-783.

Tueth, "How to manage depression and psychosis in Alzheimer's disease", Geriatrics, vol. 50, No. 1, Jan. 1995, pp. 43-49.

Ueda, et al., "Chlorpromazine reduces toxicity and $Ca^{2+}$ uptake induced by amyloid β protein (25-35) in vitro", Brain Research, vol. 748, 1997, pp. 184-188.

Wischik, et al., "Selective inhibition of Alzheimer disease-like tau aggregation by phenothiazines", Proc. Natl. Acad. Sci. USA, vol. 93, Oct. 1996, pp. 11213-11218.

I. Haller et al., "Differential neurotoxicity of tricyclic antidepressants and novel derivatives in vitro in a dorsal root ganglion cell culture model," European Journal of Anaesthesiology, vol. 24, pp. 702-708 (2007).

* cited by examiner

Trimipramine

Protriptyline

Nortriptyline

Amoxapine

Clomipramine

Figure 4.

TREATMENT OF PROTEIN AGGREGATION DISEASES

CROSS-REFERENCE TO RELATED APPLICATIONS

This is the U.S. National Stage of PCT/EP2008/051134, filed Jan. 30, 2008, which in turn claims priority to Great Britain Patent Application Nos. 0701970.6, filed Feb. 1, 007, and 0704105.6, filed Mar. 2, 2007, the entire contents of all applications are incorporated herein by reference in their entireties.

PRIOR ART SUMMARY

Alzheimer's Disease

Alzheimer's disease is a degenerative disorder of the human central nervous system that results in a progressive loss of memory and intellectual abilities. Abundant amyloid plaques and neurofibrillary tangles constitute the two major neuropathological lesions that characterise the brains of patients with Alzheimer's disease. The amyloid plaque consists mainly of a soluble polypeptide of 42-43 amino acids called beta Amyloid (or Amyloid beta). Amyloid beta is derived by an alternative cleavage of the much larger amyloid precursor protein (APP). In contrast to the plaques, the neurofibrillary tangles are formed intracellularly. Their main components are paired helical filaments (PHF) which seem to consist almost entirely of the protein tau.

Other Protein Aggregation Diseases

Prion diseases, also referred to as transmissible spongiform encephalopathies or TSEs, have only been recognised recently. Bovine spongiform encephalopathy (BSE) was first reported in 1985. The first cases of variant Creutzfeldt Jakob disease (vCJD) were reported in 1996. vCJD is a fatal neurodegenerative disease in humans believed to be caused by the consumption of BSE contaminated meat. The incubation time between infection to clinical symptoms in the human may be many years.

The only identified component of the prion, the agent causing prion diseases, is $PrP^{Sc}$, an abnormal isoform of $PrP^{C}$ ($PrP^{Sc}$ is also referred to as $PrP^{res}$ and $PrP^{C}$ also referred to as $PrP^{sen}$). $PrP^{Sc}$ has previously been regarded as being distinguished from $PrP^{C}$ in that it is comparatively protease resistant. Recently however, it has been published that there is a protease sensitive form of $PrP^{Sc}$, i.e. that there is an infective form of PrP that is protease sensitive.

It may be that the infective but protease sensitive $PrP^{Sc}$ is able to aggregate (i.e. is aggregating in nature) but not yet aggregated or at least only partially aggregated.

Both protease insensitive and protease sensitive forms of $PrP^{Sc}$ and core portions of $PrP^{Sc}$ left after partial protease digestion (often referred to in the art as $PrP^{27-30}$) are referred to herein as $PrP^{Sc}$ except where the context indicates that a specific one of these is meant. Also, the term 'aggregating proteins' is used to include both aggregated protease resistant $PrP^{Sc}$ and similar forms of other proteins as well as infective non-aggregated or partially aggregated forms of $PrP^{Sc}$ or other proteins, which may include the newly observed protease sensitive infective $PrP^{Sc}$.

$PrP^{C}$ is a GPI anchored glycoprotein of unknown function. Although some other markers for prion diseases have been suggested $PrP^{Sc}$ remains not only an obligatory prion component, but also the only reliable and universally accepted marker for this family of diseases.

Non-variant CJD is a sporadically occurring disease having similar symptoms to variant CJD.

Parkinson's disease is a degenerative condition characterised by accumulation of alpha-synuclein protein deposits and by the death of dopamine producing cells.

Huntington's Disease is an inherited neurological disorder affecting up to 8 people per 100,000. The disease is caused by a trinucleotide repeat expansion in the Huntingtin (Htt) gene and is one of several polyglutamine (or PolyQ) diseases. This expansion produces a mutant form of the Htt protein (mHtt) which forms aggregated structures, leading to neuronal cell death in specific brain regions.

The present invention relates to the treatment of all of these protein aggregation diseases. The aggregating proteins involved in these several diseases are distinct, but may be referred to by the umbrella term 'amyloid'. As discussed below, a number of proposals have been made for the use of therapeutic agents to treat such conditions, often with little or no evidence for efficacy and no demonstrated mechanism of action. In some cases, similar compounds have been proposed by different authors in the context of differing rationales.

Ueda et al (Brain Research, 748 (1997) 184-188) discloses the treatment in vitro of primary cultures of rat neurons and of rat pheochromocytoma cell line PC12 cells with a 25-35 amino acid toxic fragment of Amyloid beta protein (A beta) in a cytotoxicity assay and the effect therein of chlorpromazine, promethazine and trifluoperazine. These phenothiazines were found to reduce toxicity in both cultures. This was thought to be due to the effect of these agents on $Ca^{++}$ uptake induced by A beta. Several phenothiazines are known to have effects on $Ca^{2+}$ release or transport. These include fluphenazine, chlorpromazine and trifluoperazine, which are antagonists of calmodulin. See: —Terstappen et al; Neuropharmacology 2001 May; 40(6): 772-783. Moses et al; Exp Cell Res. 2001 Sep. 10; 269(1):88-96. Khan et al; Cell Signal 2001 January; 13(1): 57-63. Mongin et al; Am J. Physiol. 1999 October; 277(4 Pt 1):C823-32.

WO97/16191 discloses inhibiting amyloid aggregation by administration of a tricyclic family of compounds based on the 9-acridinone scaffold. These tricyclic compounds are structurally related to the phenothiazines in that they have a central ring containing a >C=O moiety where the phenothiazines have a S heteroatom in the ring.

U.S. Pat. No. 6,030,984 proposes bicyclic and tricyclic pyridone compounds for inhibiting formation of A beta peptides. However, Kuner et al (J Biological Chem; vol 275, No. 3, 21 Jan. 2000, pp 1673-78) indicates that one of these compounds accelerates A beta polymerisation.

WO02/38142 discloses treatments for mild cognitive disorder, a set of non-disease symptoms that in some cases may lead to Alzheimer's disease. These involve the administration of agents to stimulate soluble amyloid precursor protein secretion using serotoninergic drugs which include the tricyclic dibenzoazepine drugs imipramine, clomipramine and trimipramine amongst an extensive list of other drugs.

Tau protein is involved in Alzheimer's disease in forming paired helical fragments that give rise to neurofibrillary tangles. Wischik et al; Proc Natl Acad Sci USA Vol 93, 11213-11218, October 1996 Neurobiology discloses that the non-neuroleptic phenothiazine methylene blue and its desmethyl derivatives reversed the proteolytic stability of protease resistant tau protein aggregates, but the neuroleptic phenothiazine chlorpromazine was inactive.

$PrP^{res}$ is the protease resistant aggregating protein which characterises scrapie in sheep and variant CJD in humans as well as equivalent or related conditions in other mammals. Kocisko et al have disclosed (Ames conference 2004—abstract book page 49 and J Gen Virol. 2004 August; 85(Pt 8):2479-83) that certain in vitro inhibitors of the accumulation of $PrP^{res}$ can sometimes prolong the lives of scrapie-infected rodents. In vivo tests of compounds including the phenothiazine trifluoperazine failed to demonstrate prolongation of scrapie incubation periods.

Korth et al (PNAS Aug. 14, 2001, vol. 98, No. 17 9836-9841) discloses the relative activities of several phenothiazines in vitro in the inhibition of $PrP^{res}$ formation and clearance using scrapie-infected neuroblastoma cells. They concluded that substitution of the nitrogen of the central ring of the phenothiazine scaffold structure was necessary for activity. Related compounds having a different central ring with similar nitrogen substitution showed some activity. The tricyclic antimalarial drug quinacrine based on an acridine tricyclic scaffold showed greater potency. Chlorpromazine and quinacrine were proposed as drug candidates for the treatment of prion disease.

Quinacrine has since commenced clinical investigations, but Barret et al (J. Virol. August 2003, p 8462-8469) reports that whilst quinacrine had some effect on amplification of $PrP^{res}$ in an in vitro assay, melatonin, a compound binding to the A beta protein of Alzheimer's disease had no effect. This illustrates that the proteins involved in these two different protein aggregation conditions do not necessarily behave in the same way in response to drug candidates.

Variant CJD gives rise to a range of psychiatric symptoms, for some of which treatment with tricyclic antidepressants of the dibenzoazepine family are used. This has not resulted in detectable therapeutic benefit in terms of halting or reversing the progression of the underlying degenerative disease. Drugs used include clomipramine (Dervaux et al; Encephale 2001 March-April; 27(2): 194-7).

WO2004/058258 discloses compositions for treating beta amyloid related diseases including Alzheimer's disease that comprise a first component for treating the beta amyloid disease together with a second component. This second component can serve many different purposes, including being a nutritive supplement. Examples of the second agent include certain phenothiazine drugs such as fluphenazine as examples of psychotherapeutic drugs. Specifically, fluphenazine is named as an example of a suitable antipsychotic, antidepressant or psychostimulant. It is not however one of the candidates for the first component.

WO2004/045718 discloses compositions for the treatment of cognitive disorder, including Alzheimer's disease, that comprise an agent of a stated formula (preferably milnacipran) acting as a neurotransmitter reuptake inhibitor and an optional second component which may be a tricyclic dibenzoazepine such as imipramine. The function of this second agent in the composition is unstated. Whilst the proposed mechanism of action of the compositions is unclear, they do not appear to be intended to act on A beta aggregation.

Teri et al (J Geront 1991 November; 46(6): P372-7) discloses the results of a trial of imipramine in depressed and non-depressed Alzheimer's patients. Cognitive function was measured and was found to be slightly decreased upon treatment in both groups. No effects on memory were observed.

There is no good cellular model of amyloid production making the screening for potentially therapeutic compounds difficult. In addition, screening in vitro for compounds that can affect amyloid production is difficult as the unaggregated protein is immunologically not distinct from the aggregated protein. Often, compounds are screened by the ability to prevent the production of fibrils which are very large structured aggregates of the protein. However, it is becoming clear from several lines of research that it is the small early aggregates or protofibrils rather than the fibrils that are the toxic species in the amyloid pathway. Mature fibrils are inert and are not directly neurotoxic, but can at least be monitored using methods including biophysical methods (electron microscopy, atomic force microscopy and circular dichroism) and dye binding assays. All of these methods except for dye binding are cumbersome, require skilled operators and are not amenable to automation and high throughput screening. The dye assays (Thioflavin T and Congo Red) are based on the fact that the chromogenic properties of the dye change upon binding to the beta-sheet structure of amyloid fibrils. Whilst these assays can be used in high throughput screening, they lack specificity and can only detect fibrils and not the early toxic stage of aggregation producing oligomeric intermediates or protofibrils. Use of these assays in the discovery of fibril formation inhibitors may not be a good approach as fibril production may be prevented without the prevention of the production of toxic protofibril aggregates, which may actually be increased through the prevention of the removal mechanism of further aggregation.

WO 03/073106 disclosed a process (Seprion Assay) for the selective binding of an aggregating abnormal form of a protein in the presence of the non-aggregating normal form of the protein, comprising contacting under selective binding conditions a material containing both said abnormal and normal forms with a binding agent (referred to herein as the 'Seprion ligand') which is one of a number of polyionic materials having a binding avidity for said aggregating form of said protein as present in the sample. This assay has now been found to be selective for the protofibril stage of aggregation, so that a low signal is produced in the presence of non-aggregated protein or in the presence of fully aggregated protein, with a high signal being produced either when an initially non-aggregated protein begins to aggregate or when an initially aggregated protein is partially disaggregated. This has enabled us to adopt the Seprion assay as a screen for agents that are effective either to prevent aggregation or to reverse it.

Following the screening of over 100 candidate compounds we have established the identity of compounds preventing aggregation of amyloid in vitro and the identity of compounds producing disaggregation of amyloid in vitro. In vivo studies in mice have been used to demonstrate that a combination of an aggregation preventing compound and a disaggregating compound provides a synergistic benefit in therapy.

Accordingly, the present invention provides a method of treatment for the prevention or therapy of a protein aggregation disease comprising the administration in combination of a first active medicament and a second active medicament, wherein the first active medicament is active to impede aggregation of amyloid protein and the second active medicament is active to disaggregate previously formed aggregates of amyloid protein. Two or more compounds in one or both classes may of course be used in combination.

The first active medicament may be a phenothiazine-piperazine type compound and the second active medicament may be a tricyclic anti-depressant. Compounds of the phenothiazine-piperazine type may be prepared in accordance with published methods, see for instance U.S. Pat. No. 3,058,979.

Preferably, the first active medicament is a compound containing a phenothiazine or phenothiazine-like structure of the general formula 1:

wherein:

n is from 0-4;

X is N or is C;

$R_1$ and $R_2$ are single or multiple optional substitutions of their respective rings;

$R_3$ is H, or a pharmaceutically acceptable substituent;

$R_4$ is H, or a pharmaceutically acceptable substituent, or is absent according to the single or double bond nature of the C—X bond;

$R_5$ and $R_6$ independently are H, or a pharmaceutically acceptable substituent;

$R_7$ is H or a pharmaceutically acceptable substituent, or with $R_9$ forms a five or six membered saturated heterocyclic ring;

$R_8$ is H or a pharmaceutically acceptable substituent;

$R_9$ is alkyl, or a pharmaceutically acceptable substituent, or with $R_{10}$ forms an optionally N-substituted piperazine ring; and $R_{10}$ is as defined in relation to $R_9$ or is alkyl.

Preferably, in formula 1, X is N and the C—X bond is a single bond.

Alternatively, in formula 1, X is C and said C—X bond is a double bond.

Suitably, is wherein $R_{11}$ is alkyl or hydroxyalkyl, and each of the four carbon atoms of the ring may be substituted with $C_{1-3}$ alkyl.

In formula 1, $R_1$ and $R_2$ may each independently be for instance —Cl, —$CF_3$, other perfluoroalkyl, —$SO_2N(CH_3)_2$, or —$SCH_3$ and may preferably be at the 2- and or 7-positions.

Out of each pair of substituents $R_3$ and $R_4$, $R_5$ and $R_6$, and $R_7$ and $R_8$, one at least is preferably H. The other may be $C_1$-$C_3$ alkyl. Preferably, all of $R_3$, $R_4$ (when present), $R_7$, $R_8$ and one out of $R_5$ and $R_6$ are H.

$R_9$ and $R_{10}$ may each independently be $C_1$-$C_3$ alkyl, especially methyl, so that —$N(R_9)R_{10}$ may be —$N(CH_3)_2$. $R_{11}$ may be hydrogen; alkyl (e.g. methyl, ethyl, butyl, hexyl, cyclopentyl, or cyclohexyl); alicyclicalkyl of from 6-10 carbon atoms, such as cyclohexylethyl and cyclopentylmethyl; alkenyl of from 2-6 carbon atoms, such as allyl or isocrotonyl; dialkylamino-lower-alkyl, for example dimethyl- or diethyl-amino-lower-alkyl, e.g. dimethylaminobutyl and diethylaminoethyl; hydroxyl-lower-alkyl hydroxyethyl and hydroxybutyl; hydroxyl-lower-alkyl-oxy-lower-alkyl, for example beta-hydroxyethoxyethyl and beta-hydroxypropoxypropyl; monocyclic aralkyl, for example phenyl-lower-alkyl, such as benzyl, cinnamyl, phenethyl and ω-phenylbutyl; acyl such as aliphatic acyl of from 1-6, preferably 1-4 carbon atoms, for example formyl, acetyl, butyryl, propionyl, caproyl, isocaproyl, or crotonyl or equivalently halogenated derivatives of said aliphatic acyls such as chloroacetyl, trifluoroacetyl, heptafluorbutyryl and dichloroacetyl; alicyclic aliphatic acyl of from 7-10 carbon atoms, such as cyclopentylpropionyl, hexahydrobenzoyl and cyclohexylbutyryl; monocyclic aryl-aliphatic acyl of from 6-10 carbon atoms, such as cinnamoyl, phenylacetyl, phenylpropionyl or 2-furaneacrylyl; monocyclic aroyl such as furoyl or benzoyl; lower carbalkoxy, such as carbo-methoxy or carbo-ethoxy; carbobenzoxy; carbamyl and N-substituted carbamyl, for example, dialkyl such as diethyl carbamyl or dimethylcarbamyl and N-phenylcarbamyl; acyloxy-lower-alkyl, for example, aliphatic acyloxy-lower-alkyl having from 1-6, preferably 2-4 carbon atoms in the acyloxy portion, such as acetoxyethyl, crotonoyloxyethyl, butyryloxybutyl or isocaproyloxyethyl; and monocyclic aroyloxy-lower-alkyl such as benzoyloxy-lower-alkyl.

Preferably, said first active medicament is fluphenazine:

or is thioridazine:

or is prochlorperazine:

or is promazine:

or is cis-(Z)-flupenthixol:

or is cis-thiothixene:

Any suitable counter ions may be used and not just those illustrated.

Tricyclic antidepressants may be produced as described in U.S. Pat. No. 2,554,736.

The second active medicament is preferably of the general formula 2:

wherein:
Y is N—, C=, CH—, or O;
Z is =CH—, —CH$_2$—, or =N—;
R$_{13}$ is an optional pharmaceutically acceptable substituent;
R$_{14}$ is an optional pharmaceutically acceptable substituent;
R$_{15}$ is an optional pharmaceutically acceptable substituent; and
R$_{16}$ is H or is an optional pharmaceutically acceptable substituent.

R$_{13}$ and R$_{14}$, each independently, may be for instance Cl, —CF$_3$, —SO$_2$N(CH$_3$)$_2$, or —SCH$_3$ and may preferably be at the 3- and or 8-positions. Preferably, one of R$_{13}$ and R$_{14}$ is H.

R$_{15}$ is preferably a substituent group of the formula:

wherein:
each of R$_{17}$, R$_{18}$, and R$_{19}$ independently is H, or C$_{1-3}$ alkyl, or R$_{18}$, and R$_{19}$ together with N form a piperidino, morpholino, piperazine, or pyrrolidino substituent.

Optionally, Y is N and R$_{15}$ is:

Optionally, Y is Y is O and Z is =N—. Optionally, Y is C=, Z is CH$_2$, and R$_{17}$ is —CHCH$_2$CH$_2$NHCH$_3$.

The bond between positions 10 and 11 may be single or double when Z is C.

When Y is N or C, R$_{15}$ is preferably a secondary or tertiary alkylamine or alkyleneamine substituent.

R$_{16}$ may be amine, or alkylamine, or piperazinyl, or N-substituted piperazinyl.

Preferably, the second active medicament is trimipramine:

or is clomipramine:

or is nortriptyline:

or is protryptyline:

or is amoxapine:

Said treatment may be administered to a mammal that has been tested for the presence of aggregated amyloid in a sample derived therefrom and has tested positive.

The invention includes a pharmaceutical composition comprising a first active medicament and a second active medicament as defined above. Blister packs may be produced grouping formulations of the two active medicaments for administration in combination.

Further suitable combinations of compounds may now readily be identified by the use of the 'Seprion Assay' as used herein to select as first active medicaments agents giving a signal in said assay less than 100% of that given without a test compound and as second active medicaments agents giving a signal which is more than 100% of that given without a test compound. Irrespective of its actual mechanism of action, a compound shall be taken to be active to impede aggregation of amyloid protein if it gives a signal in said assay of less than 100% and shall be taken to be active to disaggregate previously formed aggregates of amyloid protein if it gives a signal in said assay of more than 100%. Thus, alternatively expressed, the invention relates to a method of treatment for the prevention or therapy of a protein aggregation disease comprising the administration in combination of a first active medicament and a second active medicament, wherein the first active medicament produces a signal of less than 100% (preferably less than 75%) in said screen and the second active medicament produces a signal of more than 100% (preferably more than 150%) in said screen.

Each selected compound should also be selected to meet requirements of pharmaceutical acceptability, such as lack of toxicity, lack of excessive side effects and so forth.

Dosage requirements for the first and second active medicaments will need to be established on a case by case basis. For the specific case of a combination of fluphenazine and trimipramine, the dose of fluphenazine may range from 0.05-5 mg/kg and the dose of trimipramine may be from 0.25-50 mg/kg. Low dosages that are active against protein aggregation diseases but are below the threshold for adverse drug reaction are preferred and can even be below the ranges suggested above. Preferred dosages may include 0.5 to 1.5 mg (e.g. 1 mg) fluphenazine and 25 to 150 mg (e.g. 50 mg) trimipramine given e.g. nocte in an adult patient. The aim is to establish a chronic low dose regimen that provides appropriate treatment for the protein aggregation disease whilst minimising or avoiding altogether the adverse drug reactions and the unwanted specific pharmacological activity of the chosen drugs.

By 'administration in combination' is meant that the two active medicaments are administered either simultaneously or else sufficiently contemporaneously that they are able to act synergistically. It will generally be sufficient that they are administered within one week of one another, but preferably they are administered within one day of each other. Periods of repeated administration of one active medicament may follow periods of repeated administration of the other. To aid administration in combination the active medicaments may be incorporated into formulations containing a mixture of the active medicaments. Alternatively, separate dosage units of each may be packaged together for convenient presentation to a patient to be taken together or one after another.

The treatment may be administered to a mammal (e.g. a human) in the absence of observable protein aggregation disease symptoms. For instance, administration may be to a mammal that has been tested for the presence of aggregated amyloid in a sample derived therefrom and has tested positive.

Said treatment may be administered to a mammal (e.g. a human) that is known to have been exposed to an infectious source of protein aggregation disease under potentially infectious circumstances. For instance, the treatment may be given to a patient known to have been exposed to contaminated blood or blood products or to have eaten or been fed contaminated (or suspected contaminated) food or feedstuffs.

Said treatment may be administered to a mammal (e.g. a human) that has been tested for a genetic predisposition to contracting a protein aggregation disease and which has tested positive.

For the monitoring of the treatment, the method may include conducting a test for the presence of a protein aggregation disease prior to, during, and/or after conducting said treatment.

Such a test may preferably comprise a 'Seprion assay' conducted on a body fluid or tissue sample.

It is considered beneficial to incorporate the medicament or medicaments into a modified release or controlled release formulation. For a patient suffering from mild cognitive disorders it would be advantageous to reduce the dosing regime to once per day to ensure full compliance. This can be achieved with an appropriate modified release oral dosage form. The requirement is to maintain a constant low level of medicament in the patient's bloodstream and consequently in the brain over extended periods to ensure disaggregation, prevention of re-aggregation of amyloid proteins and to ensure that serum levels remain well below the threshold for adverse effects. An oral modified release dosage form will provide effective treatment overnight when levels tend to fall in the bloodstream, even in the case of compounds that exhibit relatively long half-lives in the blood. If for any reason levels of the medicament or medicaments should be allowed to fall there is a danger of re-aggregation and further neuronal damage which could eventually become irreversible. This is of particular concern where low levels of medicament or medicament are being used to avoid the adverse reaction issues associated with higher doses of drug.

As an example the plasma half-life of fluphenazine hydrochloride is in the range of 2 to 12 hours and so this drug would be well suited to a modified release delivery device that maintains a sustained low concentration in plasma overnight.

The same basic advantage of sustained low level delivery of drug to the patient can also be achieved with a transdermal dosage form or an injectable bolus. The transdermal approach would be preferred here as it may be more controllable in delivering low drug doses.

Oral modified release dosage forms that achieve a sustained release profile are of several types. Diffusion-controlled products are matrix diffusion controlled systems where the therapeutic agent is dispersed in an insoluble matrix of rigid non-swellable hydrophobic materials or swellable (soluble) hydrophilic substances. Materials used for rigid matrices include insoluble plastics such as poly vinyl chloride and fatty materials such as stearic acid and bees wax. Swellable matrix systems are generally composed of hydrophilic gums of natural (guar gum, tragacanth, karaya gum), semisynthetic (hydroxy propyl methyl cellulose, carboxy methyl cellulose, xanthan gum) and synthetic (polyacrylamides) origin. The drug and matrix materials are granulated together and compressed into controlled release tablets. Drug release from insoluble matrices involves penetration of fluid, followed by dissolution of the drug particles and diffusion through fluid filled pores. In reservoir diffusion-controlled systems a core of drug is coated with the water insoluble polymer. The polymer can be applied by coating or microencapsulation techniques. The drug release mechanism across the membrane involves diffusion of water through the membrane to the inside of the core, dissolution of the drug and then diffusion of the drug into the surrounding fluid. Materials used in such devices are hydroxy propyl cellulose, ethylcellulose and polyvinyl acetate. In matrix dissolution-controlled products the drug is homogeneously dispersed throughout a matrix coated with a rate controlling membrane. Drugs which are highly water-soluble can also be formulated as modified release products by controlling their dissolution rate. Slowly soluble polymers control the rate of dissolution of the drug. Waxes such as beeswax, carnauba wax and hydrogenated castor oil have been used. The wax embedded drug is generally prepared by dispersing the drug in molten wax and congealing and granulating. In reservoir dissolution control systems the drug particles are coated or encapsulated by one of the several microencapsulation techniques with slowly dissolving materials like cellulose derivatives, poly ethylene glycols, polymethacrylates, waxes etc. The resulting reservoirs (coated beads, multi-particulate systems, pellets) may be filled as such in hard gelatin capsules (spansules) or compressed into tablets.

In erosion dosage forms the release of a drug from these products is controlled by the rate of erosion of a carrier (polymer) matrix. The rate of release (amount of drug released from the dosage form per unit of time as defined by in vitro or in vivo testing) is determined by the rate of erosion. In dissolution and diffusion controlled products (pore forming method) systems the drug core is coated with a partially soluble membrane. Pores are thus formed due to dissolution of parts of the membrane, which permit entry of aqueous medium into the core and release of dissolved drug by diffusion. Using a mixture of ethyl cellulose with poly vinyl pyrrolidone or methylcellulose, the latter material dissolves in water and forms pores in the insoluble ethyl cellulose membrane. In osmotic pump systems the driving principle is the use of osmotic pressure to release the drug at a constant rate. The rate of release of drug in these products is determined by the constant inflow of water across a semi-permeable membrane into a reservoir, which contains an osmotic agent. The drug is either mixed with the agent or is located in a reservoir. The dosage form contains a small hole from which the dissolved drug moves out at a rate determined by the rate of entrance of water due to osmotic pressure. The rate of release is constant and can be controlled within tight limits yielding relatively constant blood concentrations. The advantage of this type of product is that the release is unaltered by the environment of the device and relies simply on the passage of water into the dosage form. The rate of release can be modified by altering the osmotic agent and the size of the hole.

Drugs can also be bound to ion exchange resins and, when ingested, the release of drug is determined by the ionic environment within the gastro-intestinal tract. The drug is released slowly by diffusion mechanisms from the resin particle structure.

The invention will be further described and illustrated with reference to the following examples which make reference to the appended drawings, in which.

EXAMPLE 1

Demonstration that Both the Seprion Assay and Polyacrylamide Gel Electrophoresis can be Used to Monitor Aggregation Background Synthetic beta-amyloid peptide self-aggregates quickly once dissolved in buffer. This process was monitored by both the Seprion ligand assay which is specific for amyloid aggregates (Lane A., Stanley C. J., Dealler S., and Wilson S. M. 2003. Polymeric Ligands with Specificity for Aggregated Prion Proteins. Clin. Chem.; 49: 1774-1775) and by polyacrylamide gel electrophoresis (PAGE).

Method
1. Synthetic beta-amyloid peptide 1-40 (Sigma-Aldrich Chemical Company Ltd., A1075) was dissolved at 2.8 μg/ml in 20% trifluoroethanol and either frozen immediately or allowed to self-aggregate for 30 min at 37° C.
2. At the end of this incubation both reactions were diluted 20-fold in 50 mM Tris pH 8.3 buffer to reduce further aggregation and the reactions split.
3. One half of the reaction was assayed by the Seprion ligand assay (as described in patent WO 03073106A). Briefly, dextran polysulphate-coated microwells were used to capture the amyloid protein. The captured amyloid was then detected using an anti-beta-amyloid antibody.
4. The other half of the reaction was cross-linked with glutaraldehyde to stabilise the aggregates (as described in Bitan G., Lomakin A., and Teplow D. B. 2001. Pre-nucleation interactions revealed by photo-induced cross-linking of unmodified proteins. J. Biol. Chem.; 276: 35176-35184) and then analysed by PAGE and silver staining (as described in Antibodies: a laboratory manual, Harlow and Lane. Silver staining of gels, 1988. Cold Spring Harbor Laboratory).

Results

Figure 1:
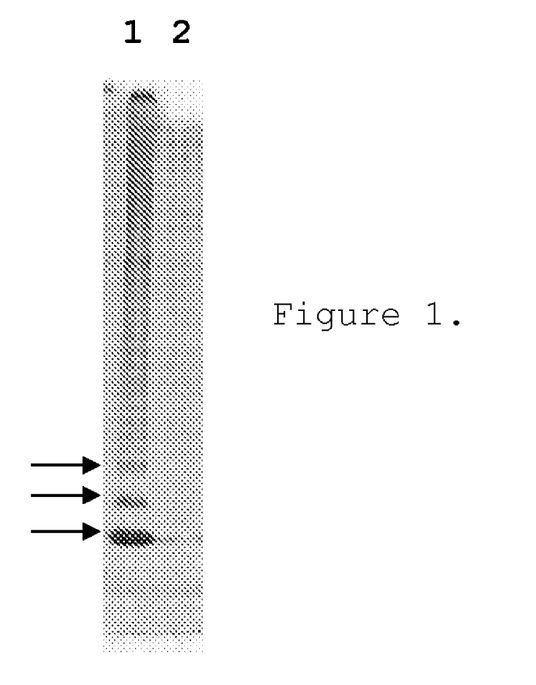
FIG. 1 shows the results obtained in Example 1 by PAGE and silver staining of unaggregated, lane 1 and aggregated, lane 2 beta-amyloid peptide.

The aggregated amyloid and unaggregated control were tested by the Seprion assay and gave signals of 0.9 and 0.15, respectively. Analysis of the same reactions by PAGE (see FIG. 1) shows the unincubated amyloid, lane 1. Monomers, dimers, trimers etc. can be seen as a ladder of bands of increasing molecular weight (marked by arrows in the figure). Lane 2 contains the incubated aggregated amyloid. It can be seen that the signal from the monomer is much reduced and no dimers, trimers or other oligomers can be observed: the aggregates in this case are so large that they cannot enter the gel matrix.

Discussion

This shows that the aggregation of the beta-amyloid peptide can be monitored both by the Seprion assay and by PAGE. In the Seprion assay, the higher signal in the incubated reaction reflects the higher degree of aggregation of amyloid peptide in that sample which could subsequently be captured by the Seprion ligand. The amyloid peptide aggregates very rapidly. Even in the process of dissolving the peptide there is some aggregation and oligomer formation. After incubation, the aggregates become so large that they do not enter the polyacrylamide gel.

EXAMPLE 2

Use of the Seprion Assay as a Rapid Screen for Compounds that Affect the Amyloid Aggregation Process Background Example 1 above demonstrates that the Seprion assay can be used to monitor the aggregation of beta-amyloid peptide. The assay was used to rapidly screen for compounds that could either interfere with or otherwise affect the aggregation process. Assays were preformed as described previously except that the amyloid peptide was incubated in the presence or absence of various test compounds.

Method
1. Synthetic beta-amyloid peptide was dissolved at 2.8 μg/ml in trifluoroethanol and either frozen immediately or allowed to self-aggregate for 30 min at 37° C. Other sets of reactions were prepared that contained the test compounds at 1 mM concentration.
2. At the end of this incubation reactions were diluted to reduce further aggregation and tested by the Seprion ligand assay.

Results

Over one hundred compounds were tested with most showing no effect on amyloid aggregation. Table 1 shows representative assay results of compounds that did exert an effect on amyloid aggregation, for example fluphenazine that decrease the signal in the incubated peptide and trimipramine that increase the signal from the aggregated peptide.

TABLE 1

Compounds that showed an effect on amyloid aggregation.

| Compound | Chemical structure | Relative aggregation compared to 'no compound' aggregation control |
| --- | --- | --- |
| Fluphenazine | Phenothiazine-piperazine | 4.37% |
| Thioridazine | Phenothiazine-(piperazine-like) | 11.9% |
| Promazine | Phenothiazine | 44.5% |
| Phenothiazine | Phenothiazine | 80% |
| Flupenthixol | (Phenothiazine-like)-piperazine | 48.2% |
| Cis-thiothixene | (Phenothiazine-like)-piperazine | 42% |
| Trimipramine | Tricyclic | 259% |
| Protriptyline | Tricyclic | 184% |
| Nortriptyline | Tricyclic | 189% |
| Amoxapine | Tricyclic | 119% |
| Clomipramine | Tricyclic | 257% |

Repeat reactions including these compounds were performed and the reactions analyzed by PAGE and silver staining as described in Example 1.

Figure 2:
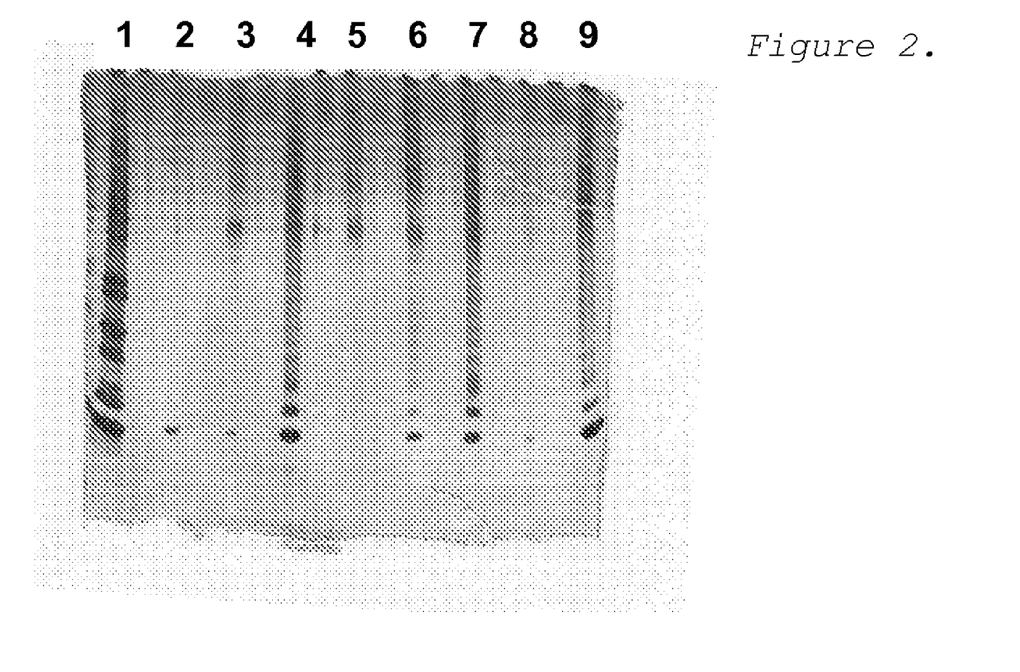
FIG. 2 shows PAGE analysis of aggregation products from Example 2. Lane 1, markers; lane 2, piracetam; lane 3, amitriptyline; lane 4, promazine; lane 5, amobarbital; lane 6, trimipramine; lane 7, fluphenazine; lane 8, aggregated control; lane 9, non-aggregated control.

The Seprion assay identified compounds that affect the aggregation of amyloid; this effect was also demonstrated by PAGE (see FIG. 2). For example, promazine, trimipramine and fluphenazine all inhibit the aggregation of the amyloid such that the peptide incubated in the presence of these compounds shows a similar silver staining pattern to the unincubated unaggregated peptide (compare lanes 4, 6 and 7 to lane 9 in FIG. 2). Compounds that showed no effect in the Seprion assay also do not inhibit the aggregation of the peptide (compare lanes 2, 3, and 5 to lane 8 in FIG. 2).

Discussion

Figure 3A:
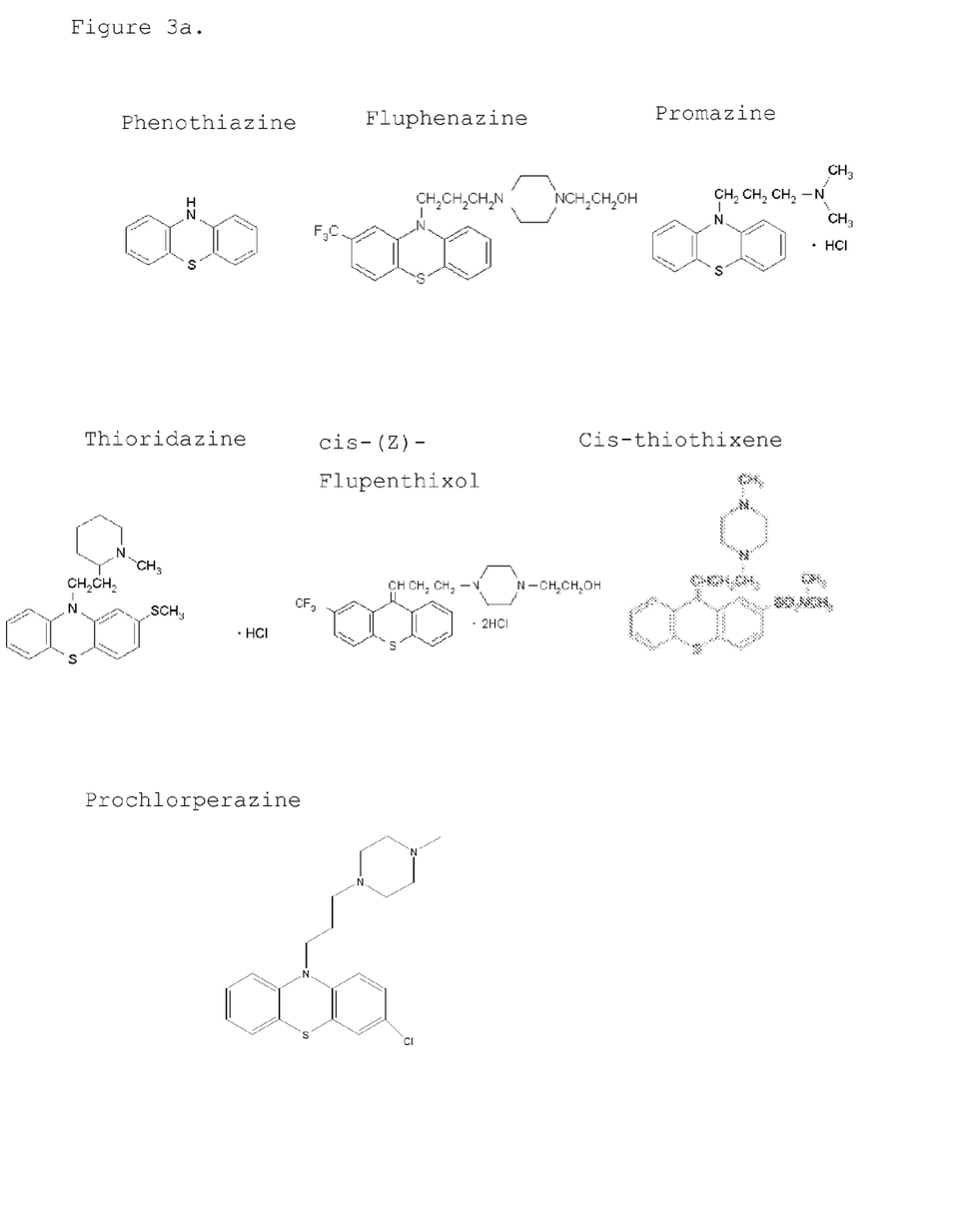
FIG. 3a shows representative phenothiazine-piperazine based compounds tested and FIG. 3b shows representative tricyclic-based compounds tested.
Figure 3B:
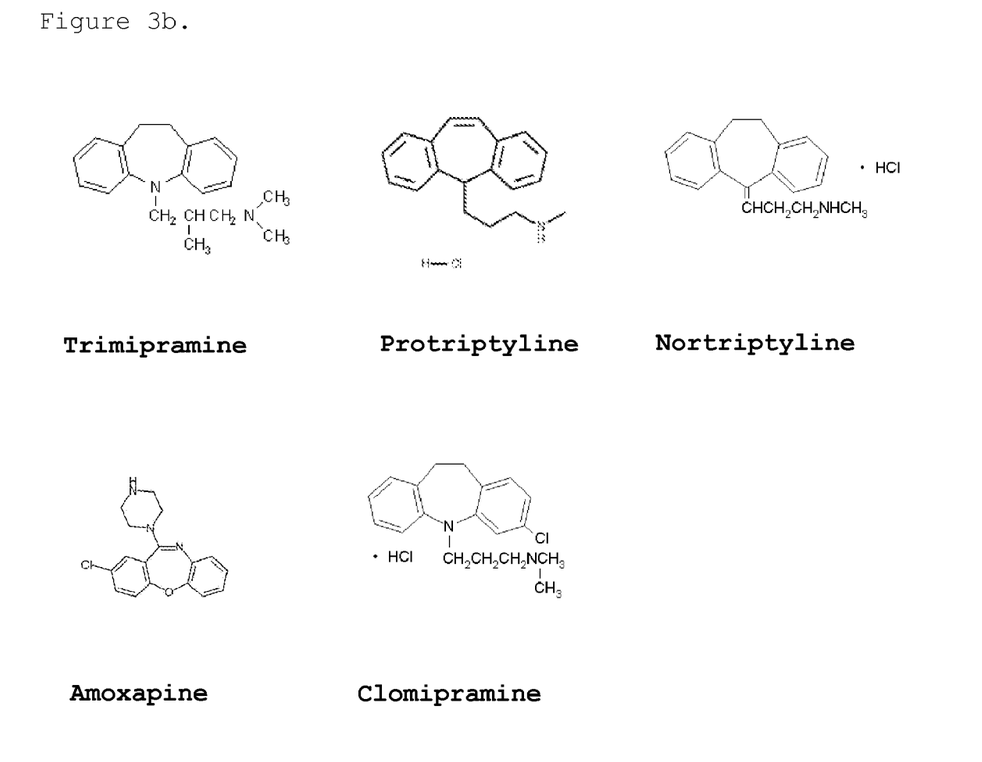

Two classes of compound were identified to have an affect on amyloid aggregation: compounds that contained a phenothiazine e.g. fluphenazine or phenothiazine-like structure e.g. flupenthixol linked to a piperazine or piperazine-like structure and compounds containing antidepressant tricyclic ring structures with a characteristic six member-seven member-six member ring configuration such as the antidepressant trimipramine (see FIGS. 3a and 3b).

The phenothiazine compounds are most effective at inhibiting aggregation when linked to a piperazine structure e.g. fluphenazine when compared to phenothiazine alone. Similar molecules where the piperazine is replaced by a ring containing a single nitrogen e.g. thioridazine or the piperazine being replaced by an alkyl group e.g. promazine are less effective. Other compounds that are similar to fluphenazine in having the piperazine-related structure but an altered phenothiazine moiety can also be partially effective e.g. flupenthixol and cis-thiothixene. It appears then, that compounds containing a similar structure to phenothiazine but having the central ring nitrogen replaced by carbon or the central ring sulphur replaced by nitrogen or carbon are also effective as long as these molecules are linked to a piperazine-like structure; for example quinacrine which is similar in structure to phenothiazine but does not have the central ring sulphur or the linked piperazine is not effective in our inhibition of aggregation studies. The antidepressant tricyclic compounds all effect the aggregation of the amyloid to some extent but those tricyclics such as trimipramine and clomipramine that link to an alkyl chain through the nitrogen of the central ring appear to be more effective. It is interesting that amoxapine is not very effective even though, similar to fluphenazine, the molecule contains a piperazine structure. This emphasises the different nature and different affect on aggregation of these two classes of compounds.

EXAMPLE 3

Determination of the Affect of Fluphenazine and Trimipramine on Amyloid Aggregation Background The signal generated in the Seprion assay is dependent upon the size of the aggregates and the accessibility of the aggregates to Seprion binding. Compounds that affect the aggregation could actually result in an increase in the Seprion signal compared to the aggregated control by generating smaller aggregates that have a higher effective molar concentration and/or are more accessible to the Seprion ligand binding. This effect could be achieved either through the breaking up of the very large aggregates to smaller aggregates or inhibition of the aggregation process so that the final aggregates themselves are smaller. Conversely, compounds that are very effective in preventing aggregation or in breaking down of the formed aggregates would lead to a much lower signal in the Seprion assay compared to the aggregated control. In this respect the effects of the two compounds. fluphenazine and trimipramine are of interest. Both show an affect on amyloid aggregation but whereas fluphenazine causes a decrease in the Seprion signal, trimipramine shows an increase. We postulate that the fact that fluphenazine and trimipramine consistently show a different effect in the Seprion monitoring of the amyloid aggregates may indicate that they act via different mechanisms. In order to test this hypothesis it was investigated to see if either compound could degrade or break up preformed amyloid aggregates.

Method
1. 10 microliters of peptide (0.5 mg/ml) were left at 37° C. for three days to aggregate.
2. The aggregated peptide was then diluted with 36 microliters of PBS and aliquotted into 10 microliters aliquots.
3. 0.5 microliters of 100 mM fluphenazine, trimipramine or piracetam were added to different aliquots and incubated overnight. One aliquot was not treated with compound to act as an aggregated control.
4. The next day the reactions were analyzed by glutaraldehyde cross-linking and PAGE as described previously.

Results

Figure 4:
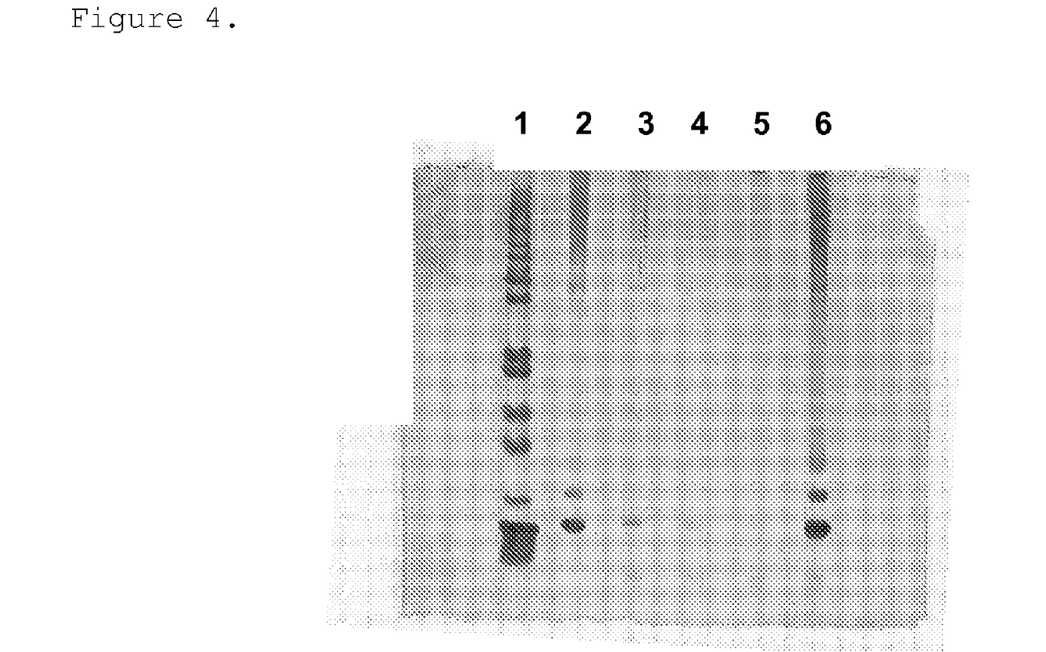
FIG. 4 shows PAGE analysis of the aggregation products from Example 3. Lane 1, markers; lane 2, fluphenazine; lane 3, trimipramine; lane 4, piracetam; lane 5, aggregated control without compound; lane 6, non-aggregated control.

FIG. 4 shows the results of the PAGE analysis. In the absence of test compound the peptide is extensively aggregated after the incubation, lane 5. This aggregated peptide is disaggregated upon subsequent incubation with fluphenazine, lane 2. Other test compounds, including trimipramine which has shown an affect on aggregation, did not have a disaggregation function, lanes 3 and 4.

Discussion

Fluphenazine and trimipramine both exert an effect on beta amyloid aggregation as measured by the Seprion assay. From the PAGE studies of the effect of these compounds it appears that fluphenazine can break down the preformed aggregates whereas trimipramine cannot. It leads from this that in the aggregation studies fluphenazine may exert its effect by inhibition of aggregation and/or dissociation of any aggregates formed whereas trimipramine may only have an inhibitory effect on aggregation. As both drugs appear to act differently to reduce amyloid aggregates it follows that studies should be performed to compare the action of both compounds in animal models of Alzheimer's Disease in order to investigate a potential synergistic effect when the compounds are used together.

EXAMPLE 4

In Vivo Testing of Drug Candidates in a Mouse Model

Background

A mouse model (hAPP(751)) that over-expresses the human beta amyloid protein with the London (717) and Swedish (670/671) mutations was used. These mice develop increased amounts of beta-amyloid 1-40 and 1-42 in the brain and develop amyloid plaques in the brain at the age of 4-6 months.

Method

Four groups of recombinant (hAPP(751)) mice were used and were treated as described below:

Group A. Control group. Daily, orally treated with saline.

Group B. Daily, orally treated with fluphenazine (0.5 mg/Kg body weight).

Group C. Daily, orally treated with trimipramine (25 mg/Kg body weight).

Group D. Daily, orally treated with both fluphenazine (0.5 mg/Kg body weight).

and trimipramine (25 mg/Kg body weight).

Treatment was started at 2 months of age and continued to 6 months of age when the mice were sacrificed and examined. The mice brains were cut in half. One half was studied by immunohistochemistry for amyloid aggregates. The other half was homogenised in TBS and the high-speed centrifugation pellets serially extracted with 1% (v/v) Triton X-100; 2% (w/v) SDS; followed by 70% formic acid. The extracts were assayed for beta-amyloid 1-40 and 1-42 by both Seprion assay (Seprion capture followed by ELISA) and by ELISA. The Seprion assay gives a measure of the amyloid aggregates whereas the ELISA measures total amyloid.

Results

The Triton extracts did not show any differences by either the Seprion assay or ELISA between the different animals. The main differences observed were in the SDS and formic acid extracts (see tables 2 and 3).

Immunohistochemistry of the brain samples showed a plaque reduction of 40, 23 and 15% in group D, B and C mice, respectively.

TABLE 2

Results of the ELISA and Seprion assay for amyloid
1-40 and 1-42 on the SDS extracts from the brains of the
treated mice.

| Animal identification | Group | Seprion assay beta-amyloid 1-40 OD420 nm | Seprion assay beta-amyloid 1-42 OD420 nm | ELISA beta-amyloid 1-40 ng | ELISA beta-amyloid 1-42 ng |
|---|---|---|---|---|---|
| 2601 | A | 1.22 | 3.07 | >300 | >800 |
| 2603 | A | >4 | >4 | >300 | >800 |
| 2605 | A | 1.26 | 1.75 | 278 | 684 |
| 2607 | A | 0.37 | 2.09 | >300 | >800 |
| 2676 | B | 0.18 | 0.93 | 88 | 295 |
| 2680 | B | 0.09 | 0.68 | 51 | 165 |
| 2593 | C | 0.11 | 0.26 | 169 | 346 |
| 2595 | C | 0.58 | 2.26 | 101 | 369 |
| 2597 | C | 0.14 | 0.98 | 195 | 529 |
| 2662 | C | 0.10 | 0.64 | 89 | 350 |
| 2666 | D | 0.06 | 0.31 | 30 | 66 |
| 2684 | D | 0.08 | 0.6 | 54 | 203 |
| 362 | D | 0.03 | 0 | 90 | 369 |

TABLE 3

Results of the ELISA and Seprion assay for amyloid
1-40 and 1-42 on the formic acid extracts from the brains of
the treated mice

| Animal identification | Group | ELISA beta-amyloid 1-40 ng | ELISA beta-amyloid 1-42 ng |
|---|---|---|---|
| 2601 | A | 549 | 308 |
| 2603 | A | 742 | 377 |
| 2605 | A | 169 | 159 |
| 2607 | A | 347 | 189 |
| 2676 | B | 116 | 143 |
| 2680 | B | 119 | 197 |
| 2593 | C | 127 | 174 |
| 2595 | C | 111 | 185 |
| 2597 | C | 182 | 311 |
| 2662 | C | 115 | 213 |
| 2666 | D | 105 | 173 |
| 2684 | D | 83 | 142 |
| 362 | D | 103 | 167 |

Discussion

The mice receiving fluphenazine or trimipramine showed a significant decrease in beta-amyloid 1-40 and 1-42 aggregate as measured by the Seprion assay of the SDS extract and a total decrease in beta-amyloid 1-40 and 1-42 load as measured by ELISA of the SDS and formic acid extracts. The mice receiving a combination of both drugs showed the biggest reduction of amyloid 1-40 and 1-42 aggregate and the largest decrease in total beta-amyloid 1-40 and 1-42. When examined by immunohistochemistry all of the treated mice showed a reduction of amyloid plaques but the largest reduction was seen in the mice treated with a combination of both drugs.

EXAMPLE 5

Effect of Anti-Amyloid Compounds on Scrapie-Infected Cell Lines

The aim of this study was to examine the effect on the prion load of scrapie infected cells of the compounds shown previously in in vitro studies to have anti-amyloid properties. The scrapie-infected mouse cell line used was ScGT1. NB4 cells were used as an uninfected control.

The ScGT1 cells are an adherent cell line grown and maintained at 37° C. under 5% carbon dioxide. The cell culture media was prepared by adding 5 ml antibiotic/antimycotic (Invitrogen 15240-062), 5 ml glutamine (Invitrogen 25030-024) and 25 ml foetal bovine serum (Invitrogen 10082-147) to a bottle (500 ml) of RPMI 1640 (Sigma R0883). The cells were maintained and passaged using standard cell culture techniques.

Effect of Fluphenazine on Scrapie-Infected Cell Lines 1 ml of 10 mM fluphenazine dihydrochloride (Sigma F4765) was prepared in 0.1 M phosphate buffer (pH 7.4). Fluphenazine dihydrochloride is acidic therefore the pH of the solution was corrected using 1 M NaOH. The fluphenazine solution was filtered using a 0.2 µM Nalgene syringe filter. This solution was stored at 4° C.

Flasks containing $1 \times 10^6$ ml ScGT1 cells were prepared and fluphenazine dihydrochloride was added at 10 µM and 1 µM final concentration. Controls were ScGT1 cells not treated with the drug and also NB4 cells. Cells were harvested as below at the start of the experiments and thereafter on a weekly basis.

Cells were harvested by discarding the culture medium and adding 3 ml TrypLE (Invitrogen 12563-011) to the flask and then returning the cells to the incubator for 5-10 min. Once the cells were floating in the trypsin solution they were transferred to a centrifuge tube (50 ml) and the volume was increased to approximately 20 mls with culture medium. The cells were centrifuged at 600-1000 RPM for 5-10 minutes, the supernatant was removed and the pelleted cells were stored at −20° C.

The prion content in the cells was determined using the assay technology and protocols described in WO03073106A2 and the components of the HerdChek BSE kit (Idexx Laboratories Inc.) Briefly the following protocol was used:

1. The frozen cell pellets were left to thaw and diluted to $1 \times 10^6$ cells/ml with deionized water.
2. 100 µl cells were mixed with 25 µl 5× Sample Capture Buffer.
3. 100 µl was added to the wells of a 96-well plate coated with the Seprion capture ligand
4. Incubated at RT for 2 hours
5. Wells were washed 3× with TBS.
6. 100 µl of conditioning agent was added and incubated for 10 mins at RT.
7. Wells were washed 3× with TBS and 100 µl anti-PrP IgM (diluted 1:1000) in TBS (containing 0.1% Tween 20, 4% BSA, 1% milk, 150 mM NaCl) was added and incubated at RT for 1 hour.
8. Wells were washed 3× in TBS (containing 0.1% Tween) and 100 ul anti-IgM alkaline phosphatase conjugate diluted 1:2500 in TBS (containing 0.1% Tween, 4% BSA, 1% milk, 150 mM NaCl) added and incubated at RT for 45 mins.
9. Wells were washed 5× in TBS (containing 0.1% Tween) and 100 ul Ampak Substrate (Oxoid, Ely, UK) added and incubated for 25 mins.
10. 100 ul Ampak Amplifier (Oxoid, Ely, UK) was then added and read at 492 nm after 10 min intervals.

Results

|  |  | Time (weeks) |  |  |  |  |
|---|---|---|---|---|---|---|
| Cell Type | Treatment | 0 | 1 | 2 | 3 | 4 |
| ScGT1 cells | 10 μM fluphenazine | 1.223 | 0.114 | 0.553 | 1.069 | 1.26 |
|  | 1 μM fluphenazine | 0.838 | No Data | 1.659 | 1.709 | 1.528 |
|  | No drug | 1.907 | 2.119 | 1.942 | 1.995 | 2.093 |
| NB4 control cells | No drug | 0.125 | 0.136 | 0.148 | 0.136 | 0.134 |

Fluphenazine was not present in the culture medium after week 1.

Effect of Drug Combinations on Scrapie-Infected Cell Lines

Drugs found to have anti amyloid properties in the in vitro assay were tested using cell culture in various combinations to determine if there were any therapeutic synergistic effects.

Drugs tested: Trimipramine, Fluphenazine, Selegaline, Methysergide and zolmitriptan. The stock drug solutions (100 μl) were prepared at 100 mM in DMSO. Filtering was omitted due to the low quantity of drugs available. Each drug was tested singly and in combination at final concentrations of 5 μM and 2.5 μM respectively in the culture media. Cells were assayed as described previously for prion content after the first passage after one week exposure to drug.

Results

| | | |
|---|---|---|
| Fluphenazine 0.867 | Trimipramine 1.197 | Zolmitriptan 1.212 |
| Selegaline 1.211 | Trimipramine + Selegaline 1.109 | ScGT1 (no drug control) 1.490 |
| Methysergide 1.282 | Trimipramine + Methysergide 1.038 | NB4 (control) 0.043 |
| Fluphenazine (repeat) 0.687 | Trimipramine + Zolmitriptan 1.118 | |
| Fluphenazine + Trimipramine 0.557 | Selegaline + Methysergide 1.338 | |
| Fluphenazine + Selegaline 1.271 | Selegaline + Zolmitriptan 1.202 | |
| Fluphenazine + Methysergide 1.061 | Methysergide 1.282 | |
| Fluphenazine + Zolmitriptan 1.148 | | |

Conclusions:

Only fluphenazine on its own and in combination with trimipramine has a significant antiprion effect on the scrapie-infected cell line. The combination treatment of fluphenazine plus trimipramine was most effective in reducing the prion content in these cells.

EXAMPLE 6

Therapy of Gerstman-Straussler-Scheinker (GSS) Syndrome

A patient, female, aged late 40s was diagnosed with an inherited prion disease; Gerstman-Straussler-Scheinker (GSS) syndrome. Mother and sister had both died with confirmed GSS. Presence of GSS disease in the patient was confirmed using chromosomal analysis of the prion gene.

At onset of symptoms the patient initially had difficulties walking or grasping objects, with rapid progression to difficulty in standing and talking. She had been treated initially with intraventricular pentosan polysulphate, which had no effect, as has been reported with other patients with GSS. Her condition continued to deteriorate with an inability to watch television, read, write or interact with other people. At this point she needed long term feeding directly into her stomach, and had a urinary catheter.

In January 2007 the patient started intragastric therapy with trimipramine and fluphenazine on a twice-daily basis. Daily dose was: trimipramine (50 mg) administered in liquid form simultaneously with fluphenazine (1 mg). No side effects were observed in the GSS patient at the lower dose used. Within 3 days of treatment it was clear that the patient had improved and began interacting with people, gradually becoming able to write and watching and understanding television. After a further 2 weeks she could speak to some degree and wanted to demonstrate her ability to move her limbs. Progress continued to take place up to around 1 month, at which point no further improvement was seen, but, at a slower pace than prior to the use of the drugs, the disease started to progress as it had originally. After 6 months her condition was still clinically superior to the one she was in prior to the use of the drug combination. The patient is still alive 12 months after commencing therapy, which would not be expected in the normal progression of this disease.

The invention claimed is:

1. A method for treatment for the therapy of a protein aggregation disease comprising the administration of a synergistic effective amount of a combination comprising a first active medicament, wherein the first medicament is fluphenazine, and a second active medicament, wherein the second medicament is trimipramine, wherein the first active medicament is administered to impede aggregation of amyloid protein and the second active medicament is administered to disaggregate previously formed aggregates of amyloid protein.

2. A method as claimed in claim 1, wherein said treatment is administered to a mammal that has been tested for the presence of aggregated amyloid in a sample derived therefrom and has tested positive.

3. A method as claimed in claim 1, wherein said treatment is administered to a mammal that is known to have been exposed to an infectious source of protein aggregation disease under potentially infectious circumstances.

4. A method as claimed in claim 1, wherein said treatment is administered to a mammal that has been tested for a genetic predisposition to contracting a protein aggregation disease and which has tested positive.

5. A method as claimed in claim 1, further comprising conducting a test for the presence of a protein aggregation disease prior to, during, and/or after conducting said treatment.

* * * * *